(12) United States Patent
Komiya

(10) Patent No.: US 8,158,778 B2
(45) Date of Patent: Apr. 17, 2012

(54) METHOD FOR THE DESALTING OF SACCHARIDE SOLUTION AND AN ANION EXCHANGER

(75) Inventor: Shinichi Komiya, Shizuoka (JP)

(73) Assignee: Mitsubishi Shoji Foodtech Co., Ltd., Tokyo (JP)

( * ) Notice: Subject to any disclaimer, the term of this patent is extended or adjusted under 35 U.S.C. 154(b) by 1763 days.

(21) Appl. No.: 10/474,744

(22) PCT Filed: Apr. 11, 2002

(86) PCT No.: PCT/JP02/03630
§ 371 (c)(1),
(2), (4) Date: Oct. 10, 2003

(87) PCT Pub. No.: WO02/083701
PCT Pub. Date: Oct. 24, 2002

(65) Prior Publication Data
US 2005/0192436 A1    Sep. 1, 2005

(30) Foreign Application Priority Data

Apr. 12, 2001 (JP) ................................. 2001-150121
Apr. 12, 2001 (JP) ................................. 2001-150122

(51) Int. Cl.
*C07H 1/00* (2006.01)
*C07H 1/06* (2006.01)
*C12H 1/04* (2006.01)

(52) U.S. Cl. ........................................ 536/124; 426/271

(58) Field of Classification Search .................. 536/124; 426/271
See application file for complete search history.

(56) References Cited

U.S. PATENT DOCUMENTS

| 3,186,940 A | * | 6/1965 | Vajna ............................. 210/677 |
| 3,558,725 A | | 1/1971 | Kohno et al. |
| 3,618,589 A | | 11/1971 | Tavani |
| 3,961,981 A | | 6/1976 | Pollio et al. |
| 3,963,789 A | | 6/1976 | Kruse et al. |
| 4,159,350 A | * | 6/1979 | Jonsson ........................ 426/271 |
| 4,322,523 A | | 3/1982 | Wagner |
| 5,118,516 A | * | 6/1992 | Shimatani et al. ............ 426/271 |

FOREIGN PATENT DOCUMENTS

| FR | 1561275 A | 3/1969 |
| GB | 569661 | 6/1945 |
| GB | 1012928 | 12/1965 |
| JP | 04-368347 A1 | 12/1992 |
| JP | 06-237782 A1 | 8/1994 |
| JP | 07-289920 A1 | 11/1995 |
| JP | 2001-096272 A1 | 4/2001 |

OTHER PUBLICATIONS

Hoell, Wolfgang et al.: "Regeneration of Anion Exchange Resins by Calcium Carbonate and Carbon Dioxide" Water Research, vol. 15, No. 8, pp. 1027-1034, 1981, XP009033101.
Adsorberharz Lewatit MP500A, Bayer AG, Jun. 1, 1971, p. 1-18.
Lewatit MP62, Bayer AG, Jul. 1, 1968, p. 1-21.
Lewatit MP64, Bayer AG, Apr. 1, 1974, p. 1-22.
Lewatit MP500, Bayer AG, Sep. 1, 1969, p. 1-28.
Submission to European Patent Office in European Patent No. 1384724 dated Jul. 20, 2009 of Opponent Cargill Incorporated.

* cited by examiner

*Primary Examiner* — Shaojia Anna Jiang
*Assistant Examiner* — Everett White
(74) *Attorney, Agent, or Firm* — Rader, Fishman & Grauer PLLC

(57) ABSTRACT

The present invention provides the means for suppressing the production of decomposition reactant, isomerization reactant, colored material, and so on when a saccharide solution is desalted, thereby suppressing the production of impurities and preventing coloration of an ion exchange resin and decrease in the desalting capacity of the ion exchange resin.

The desalting of a saccharide solution is performed by using an anion exchange resin supporting a carbonate ion and/or a hydrogencarbonate ion.

2 Claims, No Drawings

METHOD FOR THE DESALTING OF SACCHARIDE SOLUTION AND AN ANION EXCHANGER

1. TECHNICAL FIELD

The present invention relates to a method for desalting a saccharide solution and to an anion exchanger. More specifically, the present invention relates to a method for desalting saccharides or hydrogenated saccharides and to an anion exchanger used for desalting the saccharides or the hydrogenated saccharides.

2. BACKGROUND ART

Various types of salt and ion derived from reagents and catalysts used in each process, by-products produced in each process, and so forth, are contained in various saccharides obtained by providing a hydrolysis treatment on starting material such as starch, xylan, mannan, or whey, using enzyme or acid according to need, and in hydrides of saccharides obtained by hydrogenating the obtained saccharides. Accordingly, a refining process for removing the ion is essential in order to obtain products of various saccharides or hydrogenated saccharides from the starting material.

Hitherto, a method using an ion exchange resin has been generally adopted for removing ion contained in a solution of saccharides or hydrides thereof.

However, when ion is removed from the solution of saccharides or hydrides thereof as a solution to be treated by using a conventional ion exchange resin, various problems are caused in that the treated solution is colored, impurities are produced, the ion exchange resin is colored, the desalting capacity of the ion exchange resin rapidly decreases, and so on.

It is an object of the present invention to provide a new method for desalting a saccharide solution in which the above-described problems do not occur when the desalting of a solution of saccharides or hydrides thereof is performed, and an ion exchanger used for performing the method.

3. DISCLOSURE OF THE INVENTION

The inventor of the present invention eagerly studied to overcome the above-described problems and has found that a cause of the problems: the treated solution is colored, impurities are produced, the ion exchange resin is colored, the desalting capacity of the ion exchange resin rapidly decreases, and so forth during a process of desalting a saccharide solution as a solution to be treated, is that an OH type anion exchange resin used for the desalting locally increases the basic of the solution in the vicinity thereof and causes an unfavorable reaction with respect to saccharides.

That is, the inventor has found that the problems arise because various saccharides, each having a reducing group as a molecular terminal, such as glucose, xylose, maltose, oligosaccharide, and starch hydrolyzate, which are easy to produce decomposition reactant, isomerization reactant, and colored material under a basic condition, are exposed to an ion exchange resin having locally strong basic in a desalting process.

Also, a general hydrogenation of saccharides performed in an industrial scale is achieved by being heated in the existence of hydrogen gas and a catalyst. However, it is difficult to completely achieve the hydrogenation of saccharides and a small amount of non-hydrogenated saccharide remains after the hydrogenation reaction. Therefore, when an ion exchange resin is used for desalting the hydrogenated saccharides, problems of the production of decomposition reactant, isomerization reactant, colored material, and so on must be considered, as in the desalting of saccharides.

When a desalting of a saccharide solution is performed, a II-type strong basic anion exchange resin which has a low basic, is used in order to suppress the above-described unfavorable effect of an anion exchange resin on saccharides. However, these ion exchange resins also apply basic to a solution locally, and thus the problem regarding the unfavorable effect on saccharides is not sufficiently overcome. Accordingly, these ion exchange resins cannot sufficiently suppress the production of decomposition reactant, isomerization reactant, colored material, and so forth.

The inventor has supposed the causes of aforementioned unfavorable effect on saccharides and has considered various countermeasures. Then, the inventor has found that the problem, that is, the production of decomposition reactant, isomerization reactant, colored material, and so forth of saccharides at a desalting process can be significantly suppressed by using a carbonate type and/or a hydrogencarbonate type anion exchanger, more preferably, an anion exchange resin, for desalting a saccharide solution. As a result, the inventor successfully suppressed the production of impurities, prevented the coloration of an ion exchange resin, prevented decrease in the desalting capacity of the ion exchange resin, and finally completed the present invention.

That is, the means for solving the problems of the present invention are as follows.

First, a method for desalting a saccharide solution characterized in that a carbonate type and/or a hydrogencarbonate type anion exchanger is used;

Second, the method according to the first, wherein the saccharide solution is a solution of a hydrogenated saccharide;

Third, the method according to the second, wherein the solution of the hydrogenated saccharide contains a non-reactant in a hydrogenation reaction;

Fourth, a carbonate type and/or a hydrogencarbonate type anion exchanger used for desalting a saccharide solution; and Fifth, the anion exchanger according to the fourth, wherein the saccharide solution is a solution of a hydrogenated saccharide and contains a non-reactant in a hydrogenation reaction.

Examples of the saccharide solutions in the present invention include the solutions of various monosaccharides having a carbon number of 4 or more, such as erythrose, threose, ribose, arabinose, xylose, lyxose, allose, altrose, glucose, mannose, gulose, idose, galactose, and talose; oligosaccharides consist of two or more monosaccharides having a carbon number of 4 or more, such as maltose, lactose, xylobiose, maltotriose, xylotriose, maltotetraose, and isomaltose; various oligosaccharides such as malto-oligosaccharide and xylo-oligosaccharide having glucose or xylose as an constitutional unit; various polysaccharides such as dextrin, branching dextrin, cyclodextrin, starch hydrolyzate, xylan hydrolyzate, and mannan hydrolyzate; and one saccharide or mixture of two or more saccharides selected from the foregoing groups.

The saccharide solutions in the present invention include the solutions of hydrides of various saccharides obtained by hydrogenating the above-described saccharides. In particular, a saccharide solution which is produced in an industrial scale and which partly contains a non-hydrogenated saccharide can be preferably used.

The anion exchanger in the present invention should comprise material having an ion exchange capacity, and other than that, there is no limitation. Examples of such material include an ion exchange membrane, an ion exchange fibers, and an ion exchange resin. Among them, an ion exchange resin is the most preferable in terms of the simplicity in preparation of an ion exchanger and manufacturing of an ion exchange equipment.

In the present invention, it is considered that the basic in the vicinity of an anion exchanger is neutralized so as to suppress the effect on saccharides by making the anion exchanger a carbonate type and/or a hydrogencarbonate type anion exchanger by using a carbonate compound.

A strong basic anion exchanger should be used for the present invention. A saccharide solution as a solution to be treated often contains an acidulous anion such as an organic acid. Thus, the strong basic anion exchanger is more efficient of an ion exchange treatment with respect to the acidulous anion and stability at the time of a preparation of a carbonate type and/or a hydrogencarbonate type anion exchanger.

The method for using the carbonate type and/or the hydrogencarbonate type anion exchanger according to the present invention is not limited. A batch method, in which an anion exchanger is directly added to a saccharide solution as a solution to be treated, may be used. Also, a desalting may be performed by continuously feeding the solution through an ion exchange equipment in which a column is filled with an ion exchanger.

In the present invention, when a saccharide solution as a solution to be treated contacts the ion exchanger according to the present invention, the anion contained in the saccharide solution is exchanged to a carbonate ion and/or a hydrogencarbonate ion in the ion exchanger. Usually, the anion contained in a saccharide solution is an acidulous ion such as an organic acid or a strongly acidic anion. Since the acidity of the anion is higher than that of the carbonate ion and/or the hydrogencarbonate ion, the ion exchange using the ion exchanger according to the present invention can be easily performed.

As a result of the above-described ion exchange, a carbonate ion and/or a hydrogencarbonate ion exists in the treated solution. However, these ions can be easily removed as carbon dioxide gas from the saccharide solution by performing operations such as heating, concentration, depressurization, and supersonic treatment individually or by arbitrarily combining the operations.

The carbonate type and/or the hydrogencarbonate type anion exchange resin used in the present invention can be easily prepared by, for example, feeding a solution of carbonate and/or hydrogencarbonate through a column filled with a commercial Cl type anion exchange resin, or by mixing the Cl type anion exchange resin and a solution of carbonate and/or hydrogencarbonate.

The kind of carbonate and/or hydrogencarbonate used for preparing the anion exchange resin is not limited. However, sodium carbonate or sodium hydrogencarbonate is preferable in terms of simplicity in preparation. The concentration and temperature of the solution can be arbitrarily set within the range of a general preparation condition of an anion exchange resin. However, when the anion exchange resin is prepared by using a solution of hydrogencarbonate, the temperature of the solution is preferably 65° C. or less because the hydrogencarbonate ion may possibly be decomposed.

The carbonate type and/or the hydrogencarbonate type anion exchange resin may be prepared by using a sodium hydroxide solution to make an OH type anion exchange resin and then by filling carbon dioxide gas into the anion exchange resin in water.

The above-described method for preparing an anion exchange resin can be applied as a method for preparing the anion exchangers other than the anion exchange resin.

When an anion exchange resin is used as an anion exchanger, the ion contained in the saccharide solution can be removed by using the carbonate type and/or the hydrogencarbonate type anion exchange resin alone or by using the anion exchange resin with a cation exchange resin in a mixed bed.

A saccharide solution prepared under a normal preparing condition may contain various cations. In this case, the cations in the saccharide solution are preferably removed in advance by using a cation exchange resin before performing a desalting process using an anion exchange resin.

The present invention may be carried out by performing in advance refining processes such as filtration, activated carbon treatment, and carbonation, before performing the desalting of a solution to be treated using an ion exchanger.

4. ADVANTAGE OF THE INVENTION

By using a carbonate type and/or a hydrogencarbonate type anion exchanger, the production of decomposition reactant, isomerization reactant, colored material, and so on during a desalting can be significantly suppressed. Accordingly, it becomes possible to suppress the production of impurities, prevent a coloration of an ion exchange resin, and prevent a decrease in the desalting capacity of the ion exchange resin.

5. BEST MODE FOR CARRYING OUT THE INVENTION

Hereinafter, examples will follow in order to describe the present invention in detail. However, the examples do not limit the technical scope of the present invention.

EXAMPLE 1

Preparation 1 of a Hydrogencarbonate Type Anion Exchange Resin 50 ml of II-type strong basic anion exchange resin (Diaion® produced by Mitsubishi Chemical Corporation: SA20A, Cl type) was filled in a column having an internal diameter of 16 mm. Then, 100 ml of sodium hydrogencarbonate solution of 0.5 mol/L was fed through the column and the anion exchange resin was sufficiently washed by water so as to prepare a hydrogencarbonate type anion exchange resin.

EXAMPLE 2

Preparation 2 of a Hydrogencarbonate Type Anion Exchange Resin

A hydrogencarbonate type anion exchange resin was prepared under the same condition as in the Example 1, except that a weak basic anion exchange resin (Diaion® produced by Mitsubishi Chemical Corporation: WA30, Cl type) was used as an anion exchange resin.

EXAMPLE 3

Preparation 3 of a Hydrogencarbonate Type Anion Exchange Resin

A hydrogencarbonate type anion exchange resin was prepared under the same condition as in the Example 1, except that a I-type strong basic anion exchange resin (Diaion® produced by Mitsubishi Chemical Corporation: SA10A, Cl type) was used as an anion exchange resin.

REFERENCE EXAMPLE 1

Manufacture 1 of a Mixed-Bed Ion Exchange Equipment

An ion exchange equipment was manufactured in the following way so as to use a cation exchange resin and the anion exchange resin according to the present invention in a mixed-bed form.

25 ml of strongly acidic cation exchange resin (Diaion® produced by Mitsubishi Chemical Corporation: SK1B, Na type) was filled in a column having an internal diameter of 16 mm. Then, 100 ml of hydrochloric acid of 1 mol/L was fed through the column and the cation exchange resin was sufficiently washed by water so as to prepare an H type cation exchange resin.

Subsequently, the 25 ml of H type cation exchange resin and the 50 ml of hydrogencarbonate type anion exchange resin obtained in the Example 1 were mixed well in water and were filled in a jacketed column having an internal diameter of 16 mm so as to manufacture the mixed-bed ion exchange equipment. The temperature inside the jacket was warmed to 40° C.

REFERENCE EXAMPLE 2

Manufacture 2 of a Mixed-Bed Ion Exchange Equipment

A mixed-bed ion exchange equipment was manufactured in the same way as in the Reference example 1 except that the anion exchange resin prepared in the Example 2 was used instead of the anion exchange resin prepared in the Example 1. The temperature inside the jacket was warmed to 40° C.

REFERENCE EXAMPLE 3

Manufacture 3 of a Mixed-Bed Ion Exchange Equipment

A mixed-bed ion exchange equipment was manufactured in the same way as in the Reference example 1 except that the anion exchange resin prepared in the Example 3 was used instead of the anion exchange resin prepared in the Example 1. The temperature inside the jacket was warmed to 40° C.

REFERENCE EXAMPLE 4

Manufacture of a Two-Bed Ion Exchange Equipment

A two-bed ion exchange equipment comprising a resin layer filled with a cation exchange resin and a resin layer filled with the anion exchange resin according to the present invention was manufactured in the following way.

An anion exchange resin was prepared in the same way as in the Example 1 except that the amount of the anion exchange resin to be used was 60 ml.

20 ml of strongly acidic cation exchange resin (SK1B, Na type) was filled in a column having an internal diameter of 16 mm. Then, 100 ml of hydrochloric acid of 1 mol/L was fed through the column and the cation exchange resin was sufficiently washed by water so as to prepare an H type cation exchange resin.

60 ml of hydrogencarbonate type anion exchange resin was filled in a jacketed column having an internal diameter of 16 mm so as to form a resin layer of an anion exchange resin. After that, 20 ml of H type cation exchange resin was filled so that the two-bed ion exchange equipment was manufactured. The temperature inside the jacket was warmed to 36° C.

In the two-bed ion exchange equipment, the solution to be treated is fed through the cation exchange resin layer and then through the anion exchange resin layer.

※A desalting of a saccharide as a solution to be treated

PREPARATION EXAMPLE 1

Preparation 1 of a Solution to be Treated 200 g of glucose was added to 800 ml of sodium propionate solution prepared to be 0.001 mol/L so as to prepare a glucose solution having a solid content concentration of 20% by weight.

EXAMPLE 4

Method 1 for Desalting a Saccharide as a Solution to be Treated

A desalting was performed by feeding the saccharide solution prepared in the Preparation example 1 as a solution to be treated through the mixed-bed ion exchange equipment according to the Reference example 1, with a current speed of 55 ml/hr.

Two hours after the start of solution feeding through the ion exchange equipment, sampling of the desalted saccharide solution was started. The sampling was performed by taking a treated solution discharged from the ion exchange equipment in one hour as one sample. Then, from two hours to five hours after the start of solution feeding, three samples were obtained by sampling every one hour, that is, two to three hours, three to four hours, and four to five hours.

The saccharide solution obtained by the sampling was vacuum-concentrated so as to remove a dissolved carbonic acid. Then, the concentration was adjusted so that the solid content concentration becomes 20% by weight, and the pH and the electrical conductivity of the desalted saccharide solution were measured. Also, the amount of produced decomposition reactant and isomerization reactant other than glucose was measured based on the peak area by HPLC and the result was regarded as the isomerization ratio (%) from glucose. The result is shown in Table 1.

In this example, no coloration was observed in the anion exchange resin after the desalting of the saccharide solution.

EXAMPLE 5

Method 2 for Desalting a Saccharide as a Solution to be Treated

A desalting of the saccharide solution prepared in the Preparation example 1 as a solution to be treated was performed under the same condition as in the Example 4 except that the mixed-bed ion exchange equipment according to the Reference example 2 was used instead of the equipment of the Reference example 1.

The saccharide solution after the desalting was measured in the same terms as in the Example 4, and the result thereof is shown in Table 1.

In this example, no coloration was observed in the anion exchange resin after the desalting of the saccharide solution.

EXAMPLE 6

Method 3 for Desalting a Saccharide as a Solution to be Treated

A desalting of the saccharide solution prepared in the Preparation example 1 as a solution to be treated was performed under the same condition as in the Example 4 except that the mixed-bed ion exchange equipment according to the Reference example 3 was used instead of the equipment of the Reference example 1.

The saccharide solution after the desalting was measured in the same terms as in the Example 4, and the result thereof is shown in Table 1.

In this example, no coloration was observed in the anion exchange resin after the desalting of the saccharide solution.

COMPARATIVE EXAMPLE 1

Comparison with an OH Type Anion Exchange Resin

An OH type strong basic anion exchange resin was prepared in the same way as in the Example 1 except that a sodium hydroxide solution was used instead of a sodium hydrogencarbonate solution.

An ion exchange equipment was manufactured in the same way as in the Reference example 1 except that the OH type anion exchange resin was used instead of the ion exchange resin according to the present invention. Then, a desalting of the saccharide solution prepared in the Preparation example 1 as a solution to be treated was performed under the same condition as in the Example 4.

The saccharide solution after the desalting was measured in the same terms as in the Example 4 and the result is shown in Table 1.

In this example, the anion exchange resin was colored in brown after the desalting of the saccharide solution.

COMPARATIVE EXAMPLE 2

Comparison with an OH Type Anion Exchange Resin

An OH type weak basic anion exchange resin was prepared in the same way as in the Example 2 except that a sodium hydroxide solution was used instead of a sodium hydrogencarbonate solution.

An ion exchange equipment was manufactured in the same way as in the Reference example 1 except that the OH type anion exchange resin was used instead of the ion exchange resin according to the present invention. Then, a desalting of the saccharide solution prepared in the Preparation example 1 as a solution to be treated was performed under the same condition as in the Example 4.

The saccharide solution after the desalting was measured in the same terms as in the Example 4 and the result is shown in Table 1.

In this example, the anion exchange resin was slightly colored after the desalting of the saccharide solution.

COMPARATIVE EXAMPLE 3

Comparison with an OH Type Anion Exchange Resin

An OH type strong basic anion exchange resin was prepared in the same way as in the Example 3 except that a sodium hydroxide solution was used instead of a sodium hydrogencarbonate solution.

An ion exchange equipment was manufactured in the same way as in the Reference example 1 except that the OH type anion exchange resin was used instead of the ion exchange resin according to the present invention. Then, a desalting of the saccharide solution prepared in the Preparation example 1 as a solution to be treated was performed under the same condition as in the Example 4.

The saccharide solution after the desalting was measured in the same terms as in the Example 4 and the result is shown in Table 1.

In this example, the anion exchange resin was colored in brown after the desalting of the saccharide solution.

TABLE 1

The analytical result of the desalted saccharide solution

| | | Before the desalting | Sample 2 to 3 hours after solution feeding | 3 to 4 hours after solution feeding | 4 to 5 hours after solution feeding |
|---|---|---|---|---|---|
| Example 4 | Isomerization ratio (%) | 0 | <0.05 | <0.05 | <0.05 |
| | pH | 6.0 | 6.4 | 5.6 | 5.9 |
| | Electrical conductivity ($\mu$S/cm) | 60.5 | 1.80 | 1.33 | 1.57 |
| Example 5 | Isomerization ratio (%) | 0 | <0.05 | <0.05 | <0.05 |
| | pH | 6.0 | 5.5 | 5.9 | 5.3 |
| | Electrical conductivity ($\mu$S/cm) | 60.5 | 1.67 | 1.86 | 1.83 |
| Example 6 | Isomerization ratio (%) | 0 | <0.05 | <0.05 | <0.05 |
| | pH | 6.0 | 6.0 | 5.7 | 6.2 |
| | Electrical conductivity ($\mu$S/cm) | 60.5 | 0.90 | 1.13 | 1.04 |
| Comparative example 1 | Isomerization ratio (%) | 0 | 17.0 | 17.9 | 18.5 |
| | pH | 6.0 | 6.7 | 6.7 | 6.6 |
| | Electrical conductivity ($\mu$S/cm) | 60.5 | 0.57 | 0.54 | 0.48 |
| Comparative example 2 | Isomerization ratio (%) | 0 | 2.9 | 3.1 | 2.7 |
| | pH | 6.0 | 7.3 | 7.1 | 7.0 |
| | Electrical conductivity ($\mu$S/cm) | 60.5 | 1.22 | 0.90 | 0.95 |
| Comparative example 3 | Isomerization ratio (%) | 0 | 22.9 | 21.6 | 21.8 |
| | pH | 6.0 | 6.7 | 6.6 | 6.6 |
| | Electrical conductivity ($\mu$S/cm) | 60.5 | 0.64 | 0.52 | 0.55 |

From the result, the followings were confirmed: The decomposition product and the isomerization reactant of glucose are scarcely produced when the carbonate type and/or the hydrogencarbonate type anion exchange resin according to the present invention was used, compared to the case where a conventionally used OH type anion exchange resin was used. Also, the coloration of the anion exchange resin was not observed after the desalting of the saccharide solution.

It was also confirmed that the electrical conductivity indicating the residual level of ion decreased significantly compared to that before the desalting, and the desalting can be performed in the same way as a conventional one.

※A desalting of a hydrogenated saccharide as a solution to be treated

PREPARATION EXAMPLE 2

Preparation 2 of a Solution to be Treated

A glucose solution of a solid content concentration of 50% by weight was prepared, a hydrogenation reaction was performed under a hydrogen pressurization using a ruthenium catalyst, whereby a sorbitol solution was prepared.

In the sorbitol solution obtained by the reaction, non-reacted glucose was contained 0.025% by weight per the solid content.

When the sorbitol solution prepared by the hydrogenation reaction was prepared to have the solid content concentration of 20% by weight, the pH was 3.34 and the electrical conductivity was 67.7 μS/cm.

EXAMPLE 7

Method 1 for Desalting a Hydrogenated Saccharide

The saccharide solution prepared in the Preparation example 2 as a solution to be treated was desalted by feeding the solution through the two-bed ion exchange equipment according to the Reference example 4 at a current speed of 54 ml/hr.

The sampling of the desalted saccharide solution was started two hours after the start of solution feeding through the ion exchange equipment. After the sampling was started, the treated solution discharged from the ion exchange equipment in one hour was taken as a sample.

The obtained saccharide solution was vacuum-concentrated so as to remove a dissolved carbonic acid. Then, the concentration was adjusted so that the solid content concentration becomes 20% by weight, and the pH and the electrical conductivity of the desalted saccharide solution were measured. Also, a glucose content and a fructose content which is the isomerization reactant thereof were measured and the result is shown in Table 2.

COMPARATIVE EXAMPLE 4

Comparison with an OH Type Anion Exchange Resin

An OH type strong basic anion exchange resin was prepared in the same way as in the Example 1 except that a sodium hydroxide solution was used instead of a sodium hydrogencarbonate solution and the amount of the anion exchange resin was set to 60 ml.

An ion exchange equipment was manufactured in the same way as in the Reference example 4 except that the OH type anion exchange resin was used instead of the ion exchange resin according to the present invention. Then, a desalting of the saccharide solution prepared in the Preparation example 2 as a solution to be treated was performed under the same condition as in the Example 7.

The saccharide solution after the desalting was measured in the same terms as in the Example 7 and the result is shown in Table 2.

TABLE 2

The analytical result of the desalted saccharide solution

| | pH | Electrical conductivity (μS/cm) | Glucose content (% by weight) | Fructose content (% by weight) |
| --- | --- | --- | --- | --- |
| Before the desalting | 3.34 | 67.7 | 0.025 | 0 |
| Example 7 | 7.13 | 1.70 | 0.024 | <0.001 |
| Comparative example 4 | 9.35 | 2.50 | 0.018 | 0.007 |

From the result, the followings were confirmed:

In the desalting method using the carbonate type and/or the hydrogencarbonate type ion exchange resin according to the present invention, fructose, which is an isomerization reactant of glucose, is scarcely contained in the desalted saccharide solution. Also, fructose is produced in the desalted saccharide solution when a conventionally-used OH type anion exchange resin is used.

It was also confirmed that the electrical conductivity indicating the residual level of ion decreased significantly compared to that before the desalting, and the desalting can be performed in the same way as a conventional one.

※Heating tolerance test on the desalted saccharide solution

PREPARATION EXAMPLE 3

Preparation 3 of a Solution to be Treated

A glucose-containing sorbitol solution having a solid content concentration of 50% by weight, in which the sorbitol solid content in the solution is 99.75% by weight and the glucose solid content in the solution is 0.25% by weight was prepared. The solution was used as a solution to be treated.

EXAMPLE 8

The solution to be treated prepared in the Preparation example 3 was desalted by feeding the solution through the mixed-bed ion exchange equipment according to the Reference example 1 at a current speed of 55 ml/hr.

The sampling of the desalted saccharide solution was started two hours after the start of solution feeding through the ion exchange equipment. After the sampling was started, the treated solution discharged from the ion exchange equipment in one hour was taken as a sample.

The obtained saccharide solution was vacuum-concentrated so as to remove a dissolved carbonic acid. Then, the concentration was adjusted so that the solid content concentration becomes 70% by weight, and prepared a sample solution for a heating tolerance test.

The sample solution for a heating tolerance test was supplied to a pressure tight glass container and heated it with an oil bath of 145° C. for five hours so that the heating tolerance test was performed.

After the test, an analysis by a visual observation and with an absorptiometer was performed and the coloration of the sample solution was observed. The result is shown in Table 3.

COMPARATIVE EXAMPLE 5

An OH type strong basic anion exchange resin was prepared in the same way as in the Example 1 except that a sodium hydroxide solution was used instead of a sodium hydrogencarbonate solution.

An ion exchange equipment was manufactured in the same way as in the Reference example 1 except that the OH type anion exchange resin was used instead of the ion exchange resin according to the present invention.

A desalting was performed in the same way as in the Example 8 except that the saccharide solution prepared in the Preparation example 3 was used as a solution to be treated and the above-described ion exchange equipment was used. After that, the heating tolerance test was performed on the desalted saccharide solution in the same way and the result is shown in Table 3.

TABLE 3

| | | The result of heating tolerance test | |
|---|---|---|---|
| | | Absorbance (400 nm) | Visual observation |
| Example 8 | Before heating tolerance test | 0.043 | Coloration cannot be recognized visually. |
| | After heating tolerance test | 0.220 | A slight coloration in yellow was recognized. |
| Comparative example 5 | Before heating tolerance test | 0.043 | Coloration cannot be recognized visually. |
| | After heating tolerance test | 0.273 | Coloration in yellow was clearly recognized. |

The invention claimed is:

1. A method for desalting a saccharide solution, said method comprising:
    contacting a carbonate and/or a hydrogencarbonate with a strong basic anion exchanger to obtain a carbonate type and/or a hydrogencarbonate type strong basic anion exchanger,
    contacting said saccharide solution with said carbonate type and/or hydrogencarbonate type strong basic anion exchanger to desalt said saccharide solution,
    wherein the saccharide solution is a solution of a hydrogenated saccharide.

2. The method of claim 1, wherein the hydrogenated saccharide comprises hydrogenated maltose.

\* \* \* \* \*